United States Patent [19]

Pronovost

[11] Patent Number: 5,047,326
[45] Date of Patent: Sep. 10, 1991

[54] IMMUNMOLOGICAL REAGENT COMPOSITION AND ITS USE IN THE DETERMINATION OF CHLAMYDIAL OR GONOCOCCAL ANTIGENS

[75] Inventor: Allan D. Pronovost, San Diego, Calif.

[73] Assignee: Eastman Kodak Company, Rochester, N.Y.

[21] Appl. No.: 255,925

[22] Filed: Oct. 7, 1988

[51] Int. Cl.$^5$ .................. C12Q 1/00; G01N 33/53
[52] U.S. Cl. ........................................ 435/7.36; 435/28
[58] Field of Search .................. 435/4, 805, 810, 28, 435/7.36; 436/538, 533, 536, 544, 518

[56] References Cited

U.S. PATENT DOCUMENTS

| 4,404,289 | 9/1983 | Masuda et al. | 436/538 |
| 4,497,899 | 2/1985 | Armstrong et al. | 436/510 |
| 4,497,900 | 2/1985 | Abram et al. | 436/510 |
| 4,812,414 | 3/1989 | Warren et al. | 436/533 |

FOREIGN PATENT DOCUMENTS

| 0132948 | 2/1985 | European Pat. Off. . |
| 0264036 | 4/1988 | European Pat. Off. . |
| 291479 | 11/1988 | European Pat. Off. . |
| WO89/00695 | 1/1989 | PCT Int'll Appl. . |
| 58-182862 | 11/1983 | Japan . |

OTHER PUBLICATIONS

Caldwell et al., *J. Clin. Microbiol.*, 18(3), pp. 539–545 (1983).

Primary Examiner—Sam Rosen
Attorney, Agent, or Firm—J. Lanny Tucker

[57] ABSTRACT

An immunological reagent composition is useful for the determination of chlamydial or gonococcal antigens extracted from the respective organisms in a biological specimen. It is particularly useful for the determination of *Chlamydia trachomatis* or *Neisseria gonorrhoeae*. The composition comprises an antibody to a chlamydial or gonococcal antigen or an anti-antibody, a nonimmunological blocking protein having a pI from about 4 to about 7, and an amphoteric surfactant present in an amount of at least about 0.001 weight percent.

20 Claims, No Drawings

IMMUNMOLOGICAL REAGENT COMPOSITION AND ITS USE IN THE DETERMINATION OF CHLAMYDIAL OR GONOCOCCAL ANTIGENS

FIELD OF THE INVENTION

The present invention relates to an immunological reagent composition useful in the determination of chlamydial or gonococcal organisms in a biological specimen. In particular, this invention relates to a composition including a chlamydial or gonococcal antibody or anti-antibody, a blocking protein and an amphoteric surfactant.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Gonorrhea is a disease usually transmitted by sexual contact caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract detectable antigen from chlamydial organisms. See for example, U.S. Pat. Nos. 4,427,782 (issued Jan. 24, 1984 to Caldwell et al) and 4,663,291 (issued May 5, 1987 to Rose) and E.P. Publications 174,106 (Becton) and 193,431 (Caldwell et al).

Assays for *C. trachomatis* and *N. gonorrhoeae* carried out using a solid support are described in U.S. Pat. Nos. 4,497,899 and 4,497,900, respectively (both issued Feb. 5, 1985 to Armstrong et al and Abram et al, respectively). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with any material. Attachment of antigen is apparently achieved by incubating the coated support for an extended time sufficient to cause adsorption of antigen thereon (Col. 2, lines 51–55 of U.S. Pat. No. 4,497,899). The entire assay described in U.S. Pat. No. 4,497,899 takes at least 3 hours to perform. A similar but somewhat quicker assay is described in U.S. Pat. No. 4,497,900 for *N. gonorrhoeae* (see Cols. 4 and 5).

In the practice of these known assays, chlamydial or gonococcal antibodies (or anti-antibodies) are used in compositions including a nonionic surfactant and normal human serum. The normal human serum is used to reduce or "block" nonspecific interaction of the antibodies to the solid support. However, the use of this material to reduce such interactions has disadvantages, namely the cost of normal human serum, its variability in quality and the harmful pathogens it may contain. An improved "blocking" solution is highly desirable for a number of reasons.

SUMMARY OF THE INVENTION

The problems noted above are overcome with an immunological reagent composition useful for the determination of a chlamydial or gonococcal antigen comprising:

a. an antibody to a chlamydial or gonococcal antigen, or an antibody to said chlamydial or gonococcal antibody, b. a nonimmunological blocking protein having a pI from about 4 to about 7, and c. an amphoteric surfactant present in an amount of at least about 0.001 weight percent.

A method for the determination of a chlamydial or gonococcal antigen comprises:

A. contacting chlamydial or gonococcal antigen extracted from a specimen suspected of containing chlamydial or gonococcal organisms, respectively, with the immunological reagent composition described above so as to form an immunological complex of the antigen and antibody, B. prior to, simultaneously with or subsequent to the complex formation, insolubilizing either or both of the antigen or antibody on a solid support so as to form a bound immunological complex, C. separating uncomplexed materials from the bound immunological complex, and D. determining the presence of the bound complex as an indication of the amount of chlamydial or gonococcal organisms in the specimen.

The assay of this invention is rapid, reliable and simple to use. For example, it can be carried out in less than 30 minutes at room temperature. It is highly reliable for detecting extracted chlamydial antigen (such as from *C. trachomatis*), and particularly the lipopolysaccharide antigen. It can also be used to rapidly and sensitively detect a gonococcal antigen (such as from *N. gonorrhoeae*).

The assay is highly sensitive, shows low background, and nonspecific interactions between antibodies and the solid support used in the assay are greatly minimized. These advantages are achieved in the present invention from the use of an immunological reagent composition which includes a chlamydial or gonococcal antibody (or anti-antibody), a nonimmunological blocking protein which has a pI of from about 4 to about 7, and an amphoteric surfactant in the amount of at least about 0.001 weight percent

DETAILED DESCRIPTION OF THE INVENTION

The present invention is a method for determining the presence of *C. trachomatis* (or other chlamydial species), or the presence of *N. gonorrhoeae* (or other gonococcal species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing chlamydial or gonococcal organisms which comprise the chlamydial or gonococcal antigen (or mixture thereof) to be determined.

While the assay can be carried out to detect antigenic sites of whole chlamydial or gonococcal cells, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E.P. Publication 183,383 (published June 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in E.P. Publication 193,431, published Sept. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention. In still other embodiments, the invention is used to detect one or more gonococcal antigens (IA or IB proteins), or mixtures of antigens from individual gonococcal strains.

A preferred extraction composition is described in detail in copending and commonly assigned U.S. Ser. No. 255,928 filed on even data herewith by Pronovost, Mauck, Sullivan, Greer and Gilbert and entitled "High pH Extraction Composition and Its Use to Determine a Chlamydial, Gonococcal or Herpes Antigen". The central feature of that composition is the presence of an alcoholamine or salt thereof and its high pH (at least about 8). Further details of this preferred composition are provided below in relation to the examples.

In addition, it may be desirable to use a protease in the extraction procedure to break down proteins, whole blood or mucous. This is described in copending and commonly assigned U.S. Ser. No. 255,922 filed on even date herewith by Gilbert, Mauck and Stowers and entitled "Use of a Protease in the Extraction of Chlamydial, Gonococcal and Herpes Antigens".

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container, including devices specially designed for extraction of antigen. Useful devices are known in the art, including U.S. Pat. No. 4,746,614 (issued May 24, 1988 to Devaney, Jr. et al).

Preferably, the extracted antigen is detected using an immunoassay in which it is immunologically reacted with one or more appropriate antibodies. The resulting immunological complex is detected using a suitable radiometric, colorimetric, fluorometric or enzyme labeled reagent. In some cases, the reagent is a labeled antibody to the antigen, and in other cases, the labeled anti-antibody is directed to an unlabeled antibody which is reactive with the antigen. Such immunoassays generally include the formation of a detectable immunological complex on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation.

Examples of useful assays include competitive immunoassays or enzyme-linked immunoabsorbent assays (or what is commonly called "ELISA"). Such assays are described generally in U.S. Pat. No. 4,427,782 (noted above) and by Schmeer et al, *J. Clin. Microbiol.*, 15(5), pp. 830–834 (1982). The chlamydial or gonococcal antibodies used can be directed to either or several antigens being extracted from the organisms. In one embodiment, antibodies are directed to a single antigen, such as the lipopolysaccharide of the *C. trachomatis*. In other embodiments, a mixture of different antibodies is directed to several antigens, such as those extracted from several gonococcal strains.

Preferably, extracted antigen is contacted with a polymeric solid support to which it can become bound. Useful support materials include glass, cellulosic or polymeric beads, films, tubes, gels, plates and others known in the art. Preferably, the support material is a microporous membrane as described in more detail below. This membrane can be "bare", that is uncoated or untreated with any substance (as shown in U.S. Pat. No. 4,497,899, noted above). However, it is preferably treated or coated with a substance (such as a surfactant) which may enhance assay performance.

Copending and commonly assigned U.S. Ser. No. 255,922 filed on even date by myself and entitled "Determination of a Chlamydial or Gonococcal Antigen Using a Positively-Charged Ionically Binding Support" describes solid supports which have a multiplicity of positively charged groups on the surface thereof. These positively charged groups produce a positive surface charge on the support, that is, a positive zeta potential over a wide pH range. Zeta potential is known as the potential between the support and a fluid in contact with it. Any positively charged chemical radical which produces the desired zeta potential on the support is useful in the practice of this invention.

For example, the support can be constructed of any natural or synthetic polymeric material with suitable cationic groups thereon which will ionically bind to the extracted antigen. Useful polymers include polyesters, polyamides, polyethyleneimines, polycarbonates, cellulosic materials, addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary pyrimidinium salts or quaternary imidazolium salts. Quaternary ammonium salts are preferred. Further details can be obtained by consulting the application, incorporated herein by reference.

Useful polymeric solid supports include microporous membranes manufactured and sold by Pall Corp. as Posidyne® or Biodyne®-B membranes. These supports comprise a nylon membrane coated with a polyester which has quaternary ammonium groups in the pores. Other useful supports include polymeric membranes coated with surfactants.

In contrast to the embodiments described above wherein the antigen is bound to the solid support prior to immunological reaction, the assay of this invention can also be carried out by forming the immunological complex simultaneously with or prior to attachment to the solid support. In other words, the complex can be formed in solution followed by contact with the solid support for binding thereto.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in copending and commonly assigned U.S. Ser. Nos. 19,810 (filed Feb. 27, 1987 by Hinckley) and 098,248 (filed Sept. 18, 1987 by Hinckley).

Almost immediately upon contact of the antigen with the charged support, the antigen is bound to the support. If desired, any unbound antigen may be removed from the support by washing with any suitable wash solution. A particularly useful wash solution is that described and claimed in copending and commonly assigned U.S. Ser. No. 255,924 filed on even date herewith by Pronovost and Gilbert and entitled "Wash Solution Containing a Cationic Surfactant and Its Use in Chlamydial and Gonococcal Determinations". This wash solution contains a cationic surfactant. A representative solution is shown below with respect to the examples.

Within about 10 minutes, and preferably within 1 to 5 minutes, of the contact, the bound antigen is contacted with chlamydial or gonococcal antibody so as to form an immunological complex on the support. Fluid and unbound materials can be removed quickly at the same time. If the assay is carried out using a disposable test device, the support can be a microporous membrane through which fluid and unbound materials in the specimen are allowed to flow through as the antigen is bound to the membrane.

The chlamydial or gonococcal antibody can be used in the immunological reagent composition of this invention, which composition is so named because of the presence of an antibody which is considered an immunological reagent. The antibody is present in any suitable amount needed to perform the assay, and will vary depending upon the suspected amount of antigen to be detected. Generally, however, the antibody is present in an amount of at least about 1 $\mu$g/ml, and more likely from about 2 to about 10 $\mu$g/ml.

Also included in the reagent composition of this invention are one or more nonimmunological blocking proteins each of which has a pI of from about 4 to about 7. Such proteins are considered "nonimmunological" because they do not react specifically with a corresponding receptor molecule, such as an antigenic material or another protein. These proteins are "blocking" because they block sites on a solid support which might interact with the antibody. Blocking proteins useful in the practice of this invention include casein, $\alpha$-casein, porcine gamma globulin and fetal bovine serum. Others are known in the art. Mixtures can be used if so desired.

The proteins are also defined as having a pI of from about 4 to about 7. The term pI (or isoelectric point) is known as the pH at which there is an equal number of positive and negative charges in a molecule so that the molecule is neutral in charge. The pI of a protein can be measured using standard materials and procedures. For example, it can be measured by isoelectric focusing using an LKB Ampholine PAG plate (available from LKB-Produkter AB, Bromma, Sweden), pH range 3.5–9.5, and standard calibrators. The blocking protein is generally present in the composition of this invention in an amount of at least about 0.05%, and more likely from about 0.1 to about 2%, by weight.

A critical component of the immunological reagent composition of this invention is an amphoteric surfactant present in an amount of at least about 0.001%, and preferably from about 0.005 to about 2%, by weight.

Useful amphoteric surfactants are water-soluble or dispersible, compatible with immunological reagents used in the assay and inert with respect to other reagents used in the assay. By definition, the surfactant is balanced in positive and negative charges. Particularly useful classes of surfactants include, but are not limited to, those having betaine, imidazoline, sultaine or glycinate groups. Those having a betaine group are preferred.

Representative useful surfactants include fatty acid betaines (such as the Tego-Betaines TM from Goldschmidt Chemical Corp., Scherotaines TM from Scher Chemical, Inc., Emcol® 37-18, DG and NA-30 from Witco Chemical Co.), long alkyl amidoalkyl betaines (such as Jortaine TM from Jordan Chemical Co., Lexaines TM from Inolex Chemical Co., Mafo® from Mazer Chemical, Inc., Lonzaine TM C from Lonza Chemical Co.), sultaines (such as cocamidopropyl hydroxy sultaine availabe as a Jortaine TM from Jordan Chemical Co., cocamidopropyl sultaines available as Lexaine from Inolex Chemical Co.), glycinates (such as those available from Sherex Chemical Co.), sulfobetaines (such as those available from Sherex Chemical Co.), and fatty acid imidazolines (such as those available from Sherex Chemical Co. Other useful amphoteric surfactants include the Deriphats TM (from Henkel Corp.), imidazoline carboxylic acids (such as the Amphoterge® from Lonza Chemical Co.), the betaines from Hart Product Corp. (Hartaine TM CB-40), amphoteric salts (Miranol® from Miranol Chemical Co.), complex carboxylated fatty acid quaternary compounds (Sanac TM from Capital City Product Co.). Lonzaine TM C is a preferred amphoteric surfactant.

Many amphoteric surfactants meeting those requirements are known in the art, and can be evaluated by routine experimentation. The standard resource of

*McCutcheon's Emulsifiers and Detergents*, 1986 Edition, McCutcheon Division, Publishing Co., Glen Rock, N.J. 1986 can be consulted to find a number of useful amphoteric surfactants.

The composition can contain other optional components such as preservatives, antioxidants, buffers and dispersants. The composition is generally buffered to a pH of from about 6 to about 9 using any suitable buffer.

The chlamydial or gonococcal antibody used in this assay is specifically immunoreactive with one or more chlamydial or gonococcal strains (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in E.P. Publication 193,431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial or gonococcal antibody is not labeled, and detection of the antibody-antigen complex formed and bound to the support is accomplished using a second antibody (described below) which is specific to the unlabeled antibody and is appropriately labeled.

Once the bound antigen has been contacted with the chlamydial or gonococcal antibody, a bound immunological complex is formed on the support. To hasten the formation of this complex, the antibody and antigen are generally incubated at a temperature of from about 15° to about 30° C. for up to 10 minutes. Preferably, the incubation is carried out at from about 18° to about 25° C. (that is, room temperature) for from 1 to 5 minutes. These mild incubation conditions are in sharp contrast to the 30 minutes at 37° C. described as necessary for adsorption of chlamydial antigen to bare supports in U.S. Pat. No. 4,497,899 (noted above).

After the incubation and within about 10 minutes of the antibody-antigen contact, uncomplexed materials are separated from the bound complex, usually by washing one or more times with a buffered wash solution.

In the embodiment described above where the chlamydial or gonococcal antibody is labeled, the assay procedure after washing is to detect the label directly or indirectly after addition of the appropriate reagents. This is done relatively quickly after washing the bound complex, that is generally within about 10 minutes, and preferably within about 1 to about 5 minutes. If desired, label detection can be hastened with incubation if the reagents warrant it. The label is then detected using standard equipment and procedures.

In a preferred embodiment, the chlamydial or gonococcal antibody is unlabeled, and after washing the bound complex, it is contacted with an antibody directed to the unlabeled antibody. This second antibody (that is, an anti-antibody) is appropriately labeled with any of the labels described above, and can be supplied in the reagent composition of this invention having the components described herein. The antibody can be monoclonal or polyclonal and either purchased or prepared using known techniques. In a chlamydial assay, the anti-antibody is preferably a polyclonal antibody which is reactive with either of the lipopolysaccharide or major outer membrane protein antibodies.

After this contact, the resulting labeled antigen-antibody-antibody complex which is bound to the support is incubated for up to about 10 minutes at a temperature of from about 15° to about 30° C., and preferably for about 1 to about 5 minutes at from 18° to 25° C.

Separation of uncomplexed materials from the bound labeled complex is then accomplished generally by further washing using a suitable wash solution, and suitable enzyme substrates or other needed reagents are added to provide a detectable species. The bound labeled antigen-antibody-labeled antibody complex is then detected on the support using standard radiometric, colorimetric, fluorescent or other detection techniques.

A preferred method for the determination of chlamydial or gonococcal organisms comprises:

A. contacting chlamydial or gonococcal antigen extracted from a specimen suspected of containing chlamydial or gonococcal organisms, respectively, with a polymeric solid support so as to bind the antigen to the solid support, B. within about 10 minutes of the contact, contacting the bound antigen with the immunological reagent composition of this invention comprising an unlabeled chlamydial or gonococcal antibody, a blocking protein and an amphoteric surfactant as described above, so as to form an immunological complex bound to the support, C. within about 10 minutes of the antibody-antigen contact, separating uncomplexed materials from the bound immunological complex, D. contacting the bound complex with the immunological reagent composition of this invention comprising a labeled antibody to the unlabeled antibody, a blocking protein and an amphoteric surfactant as described above, so as to form a labeled antibody-antibody-antigen complex bound to the support, E. within about 10 minutes of the contact in step D, separating uncomplexed materials from the bound labeled complex, and F. determining the presence of the labeled complex on the support as a measure of the amount of chlamydial or gonococcal organisms in the specimen.

The following examples are provided to illustrate, but not limit the scope of, the present invention.

The mouse monoclonal antibody to the chlamydial lipopolysaccharide antigen was prepared using standard hybridoma technology and mouse cell line and stored in a solution of phosphate buffered saline (pH 7.4) containing 0.01% (by weight) azide.

The labeled polyclonal antibody used was a goat anti-mouse IgG antibody conjugated to horseradish peroxidase (obtained from BioRad Laboratories). This conjugate was diluted to about 1:2000 in a phosphate buffered saline solution containing 0.5% (by weight) casein and 0.01% (by weight) Lonzaine® C amphoteric surfactant, and filtered through a 0.22 μmeter filter to obtain a working solution.

An antigen extraction solution was prepared from the following components: sodium azide (25 mg in 25 ml), sodium chloride (2.5 ml of a 1.5 molar solution diluted to 25 ml), dithiothreitol reducing agent (29 mg in 25 ml), ethanolamine (6.25 ml of a 10% solution diluted to 25 ml), ethylenediaminetetraacetic acid (0.23 g in 25 ml) and sodium hydroxide (0.1 molar, pH adjusted to 12.5). To 15 ml of this solution was added 375 μl of a 10% (by weight) solution of Emcol® CC-36 cationic surfactant (quaternary ammonium chlorides of polypropoxy-t-amines, available from Witco Chemical) in methanol.

EXAMPLE 1

Immunological Reagent Composition Useful for the Determination of Chlamydial Organisms The immunological reagent composition used in the assay was prepared by adding a sample (19 μl) of the antibody solution described above to a phosphate buffered saline solution (diluting 1:800) containing casein (0.5 weight %) as a nonimmunological blocking protein and Lonzaine® C amphoteric surfactant (0.01 weight %), then filtered through a 0.22 μmeter filter to obtain a composition for use in an assay for C. trachomatis.

EXAMPLE 2

Determination of Chlamydia trachomatis Lipopolysaccharide Antigen

This example demonstrates the practice of the present invention using two antibodies, one directed against the lipopolysaccharide C. trachomatis antigen, and the second being labeled and directed to the chlamydial antibody.

The assay was carried out in a disposable test device designed similar to that described in copending and commonly assigned U.S. Ser. No. 019,810 (noted above). It contained a microporous membrane having quaternary ammonium groups on the surface (commercially available as the Pall Biodyne®-B membrane, Pall Corp.). Prior to use, the membrane was treated with Zonyl™ FSN (a nonionic fluorinated surfactant available from DuPont).

Chlamydial lipopolysaccharide antigen was extracted from elementary body protein (obtained from Professor W. J. Newhall of Indiana University) at about 20° C. for about 5 minutes using the extraction composition described above. Citrate (100 μliter of a 0.7 molar solution) was then added to lower the pH to about 7-8, followed by addition of a commercial protease (for example, protease PO652 obtained from Sigma Chemical, 400 μl of a 2 mg/ml phosphate buffered saline solution). Extraction was continued for another 5 minutes at about 20° C., after which hydrogen peroxide and sodium hydroxide (pH above 10) were added to remove endogenous catalase, peroxidase any myeloperoxidase.

The treated specimen was then filtered through a 5 micrometer membrane to remove unwanted matter. The filtered extract (120 μl) was added to a test well of the disposable test device. Specimen fluid was allowed to flow through the membrane upon contact. Within a few seconds, all fluid had drained through the membrane and the monoclonal antibody solution described above was added to the test well and allowed to drain.

The immunological complex bound to the membrane was washed twice with a wash solution (160 μl) containing Emcol® CC-9 cationic surfactant (0.75 weight %) in phosphate buffered saline solution (pH 7.2).

Immediately after the second wash, the peroxidase-labeled polyclonal antibody solution (120 μl) described above was added to the test well, and the fluid allowed to drain through immediately. Incubation at about 20° C. was carried out again for about 5 minutes to form an antigen-antibody-labeled antibody complex ionically bound to the membrane.

After washing twice with the wash solution (160 μl) described above, a dye-providing composition (120 μl) was added to the test well. This composition included hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone) (1 weight %), 4'-hydroxyacetanilide (5 mmolar) and diethylene triaminepentaacetic acid (10 mmolar).

After about 5 minutes at room temperature, a red dye was observed in the test well indicating the presence of chlamydial antigen obtained from the specimen. The entire assay after extraction of antigen was performed in less than 30 minutes.

EXAMPLE 3

Assay for LPS Antigen Using Stabilized Dithiothreitol and a Protease

This example illustrates the practice of the present invention for the determination of the lipopolysaccharide antigen of chlamydial organisms using the immunological reagent composition of this invention, Amideck™ protease (available from BioProducts Division, Eastman Kodak Company), and dithiothreitol stabilized by poly(acrylamide).

Eighteen specimens were obtained from female patients using endocervical swabs. The specimens contained considerable whole blood or mucous or both, and had been tested for the presence of C. trachomatis using standard culture techniques.

Materials Used

An extraction device like that described in U.S. Pat. No. 4,746,614 (noted above) was prepared having separate dried coatings of: (1) tris(hydroxymethyl)aminomethane buffer (from 20 μl of a 1.65 molar solution, pH 11.1) with thimerosal preservative (0.01 weight %), and (2) a mixture of dithiothreitol (0.188 molar) from a 50 μl solution containing 2-(N-morpholino)ethanesulfonic acid buffer (10 mmolar, pH 6.0), sodium azide (1.54 mmolar), ethylenediaminetetraacetic acid (5.4 mmolar) dimedone (21.4 mmolar) and poly(acrylamide) (6.35 weight %).

A protease solution was prepared having Amideck ™ protease (4 mg/ml, 170 units/mg), 2-(N-morpholino)ethanesulfonic acid buffer (10 mmolar, pH 6), sodium chloride (50 mmolar), calcium chloride (5 mmolar), 1,2-propanediol (10% w/v) and preservative (0.01 weight %).

A hydrogen peroxide solution was prepared containing 12% (by weight) hydrogen peroxide, diethylenetriaminepentaacetic acid (10 μmolar) and thimerosal preservative (0.01 weight %).

The wash solution contained 3-cyclohexylamino-2-hydroxy-1-propanesulfonic acid buffer (pH 10.0, 0.05 molar), Emcol ™ CC-9 cationic surfactant (0.75 weight %) and preservative (0.01 weight %).

A Control immunological reagent composition comprised anti-creatine kinase-MB antibodies (5 μg/ml), casein (0.5 weight %), Lonzaine ™ C amphoteric surfactant (0.01 weight %), preservative (0.01 weight %) in phosphate buffered saline solution (pH 7.2).

An immunological reagent composition was prepared containing monoclonal antibodies to the lipopolysaccharide antigen (4 μg/ml) supplied in phosphate buffered saline solution (pH 7.2) containing casein, Lonzaine ™ C amphoteric surfactant and preservative as noted above in the Control composition.

Goat anti-mouse IgG antibodies conjugated to horseradish peroxidase (conjugate available from Bio-Rad) (1:700 dilution) were supplied in phosphate buffered saline solution (pH 7.2) containing casein, Lonzaine ™ C amphoteric surfactant and preservative as noted above as well as 4'-hydroxyacetanilide (10 mmolar).

A leuco dye composition contained 2-(4-hydroxy-3-methoxyphenyl)-4,5-bis(4-methoxyphenyl)imidazole leuco dye (0.008 weight %), poly(vinylpyrrolidone) (1 weight %), sodium phosphate buffer (pH 6.8, 10 mmolar), diethylenetriaminepentaacetic acid (10 μmolar), 4'-hydroxyacetanilide (2 mmolar) and hydrogen peroxide (10 mmolar).

Assay

The assay was performed as follows for each of the eighteen specimens obtained using a separate test device for each specimen. The protease solution (about 280 μl) was added to the extraction device and a patient swab was placed therein, rotated for 5-10 seconds, followed by incubation for 3 minutes at room temperature (that is, 18°-22° C.).

The extraction solution (about 280 μl) was then added to the device containing the swab which was then rotated for another 5-10 seconds followed by incubation at room temperature for 3 minutes.

The hydrogen peroxide solution was added to the device and the same procedure was repeated.

The resulting solution in the extraction device was then removed from the device using a pipette, prefiltered and transferred to each well of a disposable test device like those described in U.S. Ser. No. 019,810 (noted above), adding about 160 μl to each well. One well (#1) of each test device was considered a Control well while two others (#2 and #3) were considered test wells. The vent in the device was opened allowing drainage of all fluids. Each well was then washed with the wash solution described above (160 μl) with drainage.

The Control antibody solution (about 80 μl) was added to well #1 while the lipopolysaccharide antibody solution (about 80 μl) was added to each of wells #2 and #3 without drainage. Incubation at room temperature was carried out for 2 minutes.

After drainage, the wash step was repeated, and the peroxidase-labeled anti-antibody solution (about 80 μl) was added to all wells without drainage, followed by incubation at room temperature for 5 minutes.

Following drainage and another wash step, the leuco dye composition was added to each well without drainage. After incubation at room temperature for 5 minutes, dye formation was stopped by the addition of 0.01% sodium azide solution (about 120 μl) to each well and drainage. The dye formed on the membrane of each well was observed visually and graded (0 to 10, with 0 representing no color). The results are provided in the following Table I which compares the assay results to those found with the standard culture techniques. It can be seen that the assay was highly accurate, determining all negative specimens and 83% of the positive specimens.

TABLE I

| Specimen | Culture Results | Visual Readings | | | Assay +/− |
|---|---|---|---|---|---|
| | | Control | Well #2 | Well #3 | |
| 1 | Positive | 2-3 | 4 | 4 | Positive |
| 2 | Negative | 1-2 | 1-2 | 1-2 | Negative |
| 3 | Negative | 2 | 2 | 2 | Negative |
| 4 | Negative | 1 | 1 | 0-1 | Negative |
| 5 | Positive | 1 | 10 | 10 | Positive |
| 6 | Negative | 1-2 | 0-1 | 0-1 | Negative |
| 7 | Positive | 1 | 10 | 10 | Positive |
| 8 | Negative | 2-3 | 2 | 2 | Negative |
| 9 | Positive | 1 | 6 | 6 | Positive |
| 10 | Positive | 1-2 | 5 | 5 | Positive |
| 11 | Positive | 1-2 | 1 | 1 | Negative |
| 12 | Positive | 6 | 7 | 7 | * |
| 13 | Positive | 1 | 5-6 | 5-6 | Positive |
| 14 | Positive | 1 | 7-8 | 7-8 | Positive |
| 15 | Positive | 1 | 10 | 10 | Positive |
| 16 | Positive | 1 | 9 | 9 | Positive |
| 17 | Positive | 1 | 5-6 | 5-6 | Positive |
| 18 | Positive | 1 | 1 | 0-1 | Negative |

*No test, that is, assay procedure was done incorrectly.

EXAMPLE 4

Assay for Chlamydial Antigen Using a Labeled Chlamydial Antibody

This example illustrates an assay for *C. trachomatis* using a labeled chlamydial antibody and an immunological reagent composition of this invention. Two different antibodies directed to the major outer membrane protein (MOMP) were conjugated to horseradish peroxidase by a known method (Yoshitake, *Eur. J. Biochem.*, 101, 395, 1979). The conjugates were kept in phosphate buffered saline solution (pH 7.4) containing 0.01% (by weight) thimerosal until used in the assay.

Serovar H antigen elementary bodies were obtained from Professor W. J. Newhall of Indiana University. Chlamydial MOMP antigen was extracted for 5 minutes at room temperature to prepare solutions of extracted antigen having antigen final concentrations of 1500 and 4500 pg.

Hydrogen peroxide (1.5 ml of 8% solution) was added to each antigen extract solution, mixed and kept at room temperature for 5 minutes.

The solutions (120 μl) were then added to disposable test devices containing Biodyne® nylon microporous membrane which had been precoated with Zonyl™ FSN surfactant (0.05%, by weight), and allowed to flow through.

The peroxidase-labeled antibodies (conjugates 1 and 2) were added in either of two immunological reagent compositions of this invention (120 μl) containing casein and Lonzaine® amphoteric surfactant as follows: composition 1 contained 1.25% (by weight) casein and 0.025% (by weight) surfactant, and composition 2 contained 2% (by weight) casein and 0.04% (by weight) surfactant. Incubation for 5 minutes at room temperature followed.

The membranes were then washed twice with a phosphate buffered saline solution (160 μl) containing Emcol® CC-9 cationic surfactant (0.75 weight %).

Leuco dye solution (120 μl) was added to the test devices, incubation followed for 10 minutes at room temperature and the dye density was then determined.

A Control solution containing no antigen was similarly tested to indicate background density.

The results are shown in Table II below as the difference in transmission density ($\Delta D_T$) between the test solutions and the Control solution.

TABLE II

| Antigen Concentration (pg) | $\Delta D_T$ Antibody Conjugate 1 | Antibody Conjugate 2 |
|---|---|---|
| 1500 | 0.094 | 0.081 |
| 4500 | 0.194 | 0.182 |

The invention has been described in detail with particular reference to preferred embodiments thereof, but it will be understood that variations and modifications can be effected within the spirit and scope of the invention.

I claim:

1. An immunological reagent composition useful for the determination of a chlamydial or gonococcal antigen comprising:
   a. an antibody to a chlamydial or gonococcal antigen, or an antibody to said chlamydial or gonococcal antibody,
   b. a nonimmunological blocking protein having a pI of from about 4 to about 7, and
   c. an amphoteric surfactant present in an amount of at least about 0.001 weight %.

2. The composition of claim 1 wherein said amphoteric surfactant is present in an amount of from about 0.005 to about 2 weight %.

3. The composition of claim 1 wherein said surfactant has a group selected from the group consisting of a betaine, imidazoline and sultaine.

4. The composition of claim 3 wherein said surfactant contains a betaine group.

5. The composition of claim 4 wherein said surfactant is a lauramidoalkyl or cocamidoalkyl betaine.

6. The composition of claim 1 wherein said protein is selected from the group consisting of casein, α-casein, porcine gamma globulin and fetal bovine serum.

7. The composition of claim 1 comprising a labeled anti-antibody.

8. The composition of claim 1 wherein said chlamydial or gonococcal antibody is labeled.

9. A method for the determination of a chlamydial or gonococcal antigen comprising:
   A. contacting chlamydial or gonococcal antigen extracted from a specimen suspected of containing chlamydial or gonococcal organisms, respectively, with an immunological reagent composition comprising:
      a. an antibody to a chlamydial or gonococcal antigen,
      b. a nonimmunological blocking protein having a pI of from about 4 to about 7, and
      c. an amphoteric surfactant present in an amount of at least about 0.001 weight %,
      so as to form an immunological complex of said antigen and antibody,
   B. prior to, simultaneously with or subsequent to said complex formation, insolubilizing either or both of said antigen or antibody on a solid support so as to form a bound immunological complex,
   C. separating uncomplexed materials from said bound immunological complex, and
   D. determining the presence of said bound complex as an indication of the amount of chlamydial or gonococcal organisms in said specimen.

10. The method of claim 9 wherein said chlamydial or gonococcal antibody is labeled.

11. The method of claim 10 wherein said antibody is labeled with an enzyme.

12. The method of claim 9 wherein said chlamydial or gonococcal antibody is unlabeled, and said bound unlabeled antibody-antigen complex is reacted with a labeled anti-antibody,
    said labeled anti-antibody being supplied in admixture with a nonimmunological blocking protein having a pI of from about 4 to about 7, and an amphoteric surfactant present in an amount of at least about 0.001 weight %.

13. The method of claim 9 for the determination of a chlamydial antigen.

14. The method of claim 9 for the determination of a gonococcal antigen.

15. A method for the determination of chlamydial organisms comprising:
    A. contacting chlamydial antigen extracted from a specimen suspected of containing chlamydial organisms, with a polymeric solid support so as to bind said antigen to said solid support,
    B. within about 10 minutes of said contact, separating said specimen from said bound antigen and contacting said bound antigen with an immunological reagent composition comprising:
       a. an unlabeled antibody to said chlamydial antigen,
       b. a nonimmunological blocking protein having a pI of from about 4 to about 7, and
       c. an amphoteric surfactant present in an amount of at least about 0.001 weight %,
       so as to form an immunological complex bound to said support,
    C. within about 10 minutes of said antibody-antigen contact, separating uncomplexed materials from said bound immunological complex,
    D. contacting said bound complex with an immunological reagent composition comprising
       a. a labeled antibody to said unlabeled antibody, b. a nonimmunological blocking protein having a pI of from about 4 to about 7, and c. an amphoteric surfactant present in an amount of at least about 0.001 weight %, so as to form a labeled antibody-antibody-antigen complex bound to said support, E. within about 10 minutes of said contact in step D, separating uncomplexed materials from said bound labeled complex, and F. determining the presence of said labeled complex on said support as a measure of the amount of chlamydial organisms in said specimen.

16. The method of claim 15 wherein said surfactant has a group selected from the group consisting of a betaine, imidazoline and sultaine.

17. The method of claim 16 wherein said surfactant is a lauramidoalkyl or cocamidoalkyl betaine.

18. The method of claim 16 wherein said protein is selected from the group consisting of casein, α-casein, porcine gamma globulin and fetal bovine serum.

19. The method of claim 16 carried out with a microporous membrane in a disposable test device.

20. The method of claim 16 wherein said antibody label is peroxidase, and said determination of said labeled complex is accomplished with a reagent composition which provides a dye in the presence of peroxidase and hydrogen peroxide.

* * * * *